United States Patent

Holm

Patent Number: 5,605,541
Date of Patent: Feb. 25, 1997

[54] FIBRIN SEALANT APPLICATOOR

[75] Inventor: Niels-Erik Holm, Birkerod, Denmark

[73] Assignee: E. R. Squibb and Sons, Inc., Princeton, N.J.

[21] Appl. No.: 351,867

[22] Filed: Dec. 8, 1994

[51] Int. Cl.⁶ .................................................. A61M 37/00
[52] U.S. Cl. ................................ 604/82; 604/68; 604/70
[58] Field of Search ............................. 604/68, 69, 70, 604/72, 82, 310, 57; 128/200.14, 200.18, 200.19; D9/448; D23/224, 226; 239/422, 423, 424

[56] References Cited

U.S. PATENT DOCUMENTS

| | | | |
|---|---|---|---|
| 3,223,083 | 12/1965 | Cobey . | |
| 3,577,516 | 5/1971 | Gould et al. . | |
| 4,022,379 | 5/1977 | Ladisch | 239/8 |
| 4,095,929 | 6/1978 | McCartney | 431/19 |
| 4,263,346 | 4/1981 | Sandell | 427/196 |
| 4,359,049 | 11/1982 | Redl et al. . | |
| 4,525,175 | 6/1985 | Stellaccio | 48/86 R |
| 4,631,055 | 12/1986 | Redl et al. . | |
| 4,735,616 | 4/1988 | Eibl et al. . | |
| 4,902,281 | 2/1990 | Avoy . | |
| 4,907,961 | 3/1990 | Anderson | 431/8 |
| 4,978,336 | 12/1990 | Capozzi et al. . | |
| 5,226,877 | 7/1993 | Epstein . | |
| 5,368,563 | 11/1994 | Lonneman et al. . | |

FOREIGN PATENT DOCUMENTS

| | | |
|---|---|---|
| 0592242 | 10/1993 | European Pat. Off. . |
| 9407420 | 9/1992 | Japan . |

Primary Examiner—Corrine M. McDermott
Assistant Examiner—N. Kent Gring
Attorney, Agent, or Firm—Theodore R. Furman, Jr.; John M. Kilcoyne

[57] ABSTRACT

A novel device and method for the application of two or more components of a fibrin sealant using a gas is disclosed. The novel device and method involve the concentric arrangement of annular apertures for each of the components concentric with and radially outward of a center gas discharge aperture in the exit end of a spray head. Reservoirs for each component, for example syringe cartridges or cylinders, are in dextrete fluid communication with the spray head and preferably can be activated by a common means.

3 Claims, 2 Drawing Sheets

FIBRIN SEALANT APPLICATOOR

BACKGROUND OF THE INVENTION

Inventor: Niels Erik Holm

U.S. Pat No. 4,359,049 to Redl discloses a double barrel syringe which reportedly is useful for applying a tissue adhesive such as fibrin glue or fibrin sealant to a human or animal in need thereof. The fibrin sealant described comprises predominantly two major components, a fibrinogen-containing component and a thrombin-containing component, each in liquid form upon use. Essentially, the thrombin and fibrinogen, when mixed, provide that the peptide claims of the fibrinogen are cleaved and conditions are provided so that the resulting fibrin polymerizes into a clot which is useful for sealing fluid and air leaks, in hemostasis and to connect tissue. To avoid premature clot formation double-barrelled applicators are employed which, of course, keep the two components separate until application to a patient is required. The '049 patent discloses that pistons within the two cartridges, each containing one component, can be commonly actuated to dispense fluid simultaneously from each. Typically, the barrels or cartridges are connected to a spray head.

Other prior art patents describe various mixing loads for mixing two or more components used in these and other surgical sealants. For example, U.S. Pat. No. 5,116,315 assigned to Hemaldics describes a head where the liquid conducts leading from the component cartridges enter a mixing chamber fashioned so as to provide a swirling of the components before they exit a common exit channel. Adequate mixing of the components is desired so as to form a uniform fibrin sealant. Inefficient mixing results in the coadministration of fibrinogen and thrombin which may only result in a small yield of actual sealant. A difficulty with fibrin sealant applicators can be the premature formation of the clot within the device, especially those devices where the components are mixed within a mixing head and/or those devices wherein the components exit through a common channel. After the first spray of sealant is complete a clot may block the exit channels rendering the applicator useless and greatly reducing the surgeon's flexibility in carrying out the sealant part of the surgical procedure.

U.S. Pat. No. 4,631,055 to Immuno includes a gas conveying channel for blowing a gas through the needle or mixing head during discharge of the components. However, an even, uniform distribution of the materials over the anatomical area of interest is still not achieved. Indeed, a significant amount of the components are wasted.

EP 592 242 to Edwardson et al. discloses the first completely autologous fibrin sealant. It provides for the coadministration of a fibrin monomer solution with a buffer solution conducive to polymerization of the fibrin monomer thereby providing clot formation. The fibrin monomer can be prepared in less than 30 minutes from a single source of blood (preferably that of the patient to receive the sealant). This breakthrough technology provides a fixed amount of fibrin monomer solution from a sample of about 140–160 ml of blood. Uniform and efficient mixing is even more important in order to benefit from this safe, efficient, autologous sealant product and therefore new devices and methods for applying two or more components to form a surgical sealant would be useful addition to the art.

SUMMARY OF THE INVENTION

In accordance with the present invention a novel device and method for applying components of a fibrin sealant are described. The device comprises a source of a gas and reservoir for each component wherein the gas source and component reservoirs can be actuated by common means. Each of the reservoirs and gas source are separately in fluid communication with a spray head having a center aperture or its exit end and annular apertures, concentric with and radially outward from the center aperture whereby the gas and each of said components are discharged through separate apertures. Preferably, the gas is discharged through the center aperture and the fibrin sealant forming components are discharged separately through each of the annular apertures.

DETAILED DESCRIPTION OF THE PREFERRED EMBODIMENTS

The present invention provides an extremely efficient mixing of fibrin sealant forming components outside of the spray head of the applicator which thereby provides for an economical use of each components and eliminates problems of applicator clogging. The device incorporates a novel spray head having a central aperture and two or more concentric annular apertures, radially outward of the central aperture, for each of the fibrin sealant-forming components. This spray head can be used with any convenient arrangement of sources of the desired gas and components. Typically, the components are each loaded into a syringe cartridge and such cartridges containing the desired components may advantageously be arranged in a parallel fashion. The cartridges arranged as such are preferably commonly held and can be actuated by common means, e.g., a trigger or plunger to commonly actuate pistons within each cartridge. The source of gas can be a line from a remote source or an additional cartridge or reservoir within, or attached to, the applicator, as desired. The gas is typically actuated in a common manner with the component actuation although optional independent gas actuation, in addition to common actuation, may be advantageous. Separate channels provide fluid communication from each component and gas source to the sprayhead.

The fibrin sealant components are those known in the prior art. Suitable fibrinogen-containing components and thrombin-containing components are described in U.S. Pat. No. 5,116,315, and the like. The disclosures of these documents are incorporated herein by reference. Preferably the fibrin sealant components of EP 592 242 are used, i.e., a fibrin monomer-containing solution and a solution which provided for the polymerization and preferably crosslinking of the monomer into a fibrin clot. This is typically a buffer solution to raise the pH of the fibrin monomer solution. Suitably a pH 10 buffer (acetate) containing a source of calcium ions is employed. The disclosure of EP 592 242 is also incorporated herein by reference. Any gas can be used such as Argon, $CO_2$, air, Nitrogen and the like.

Figure 1:
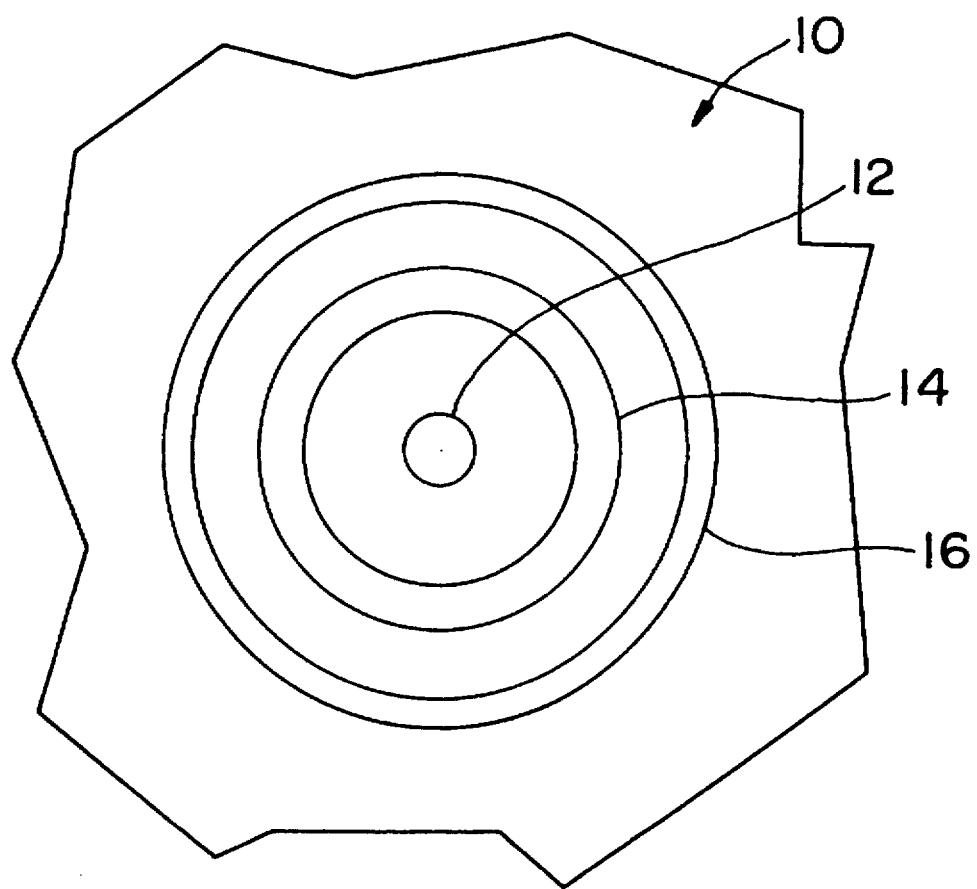
FIG. 1 is an end view of the exit end of the present spray head.
Figure 2:
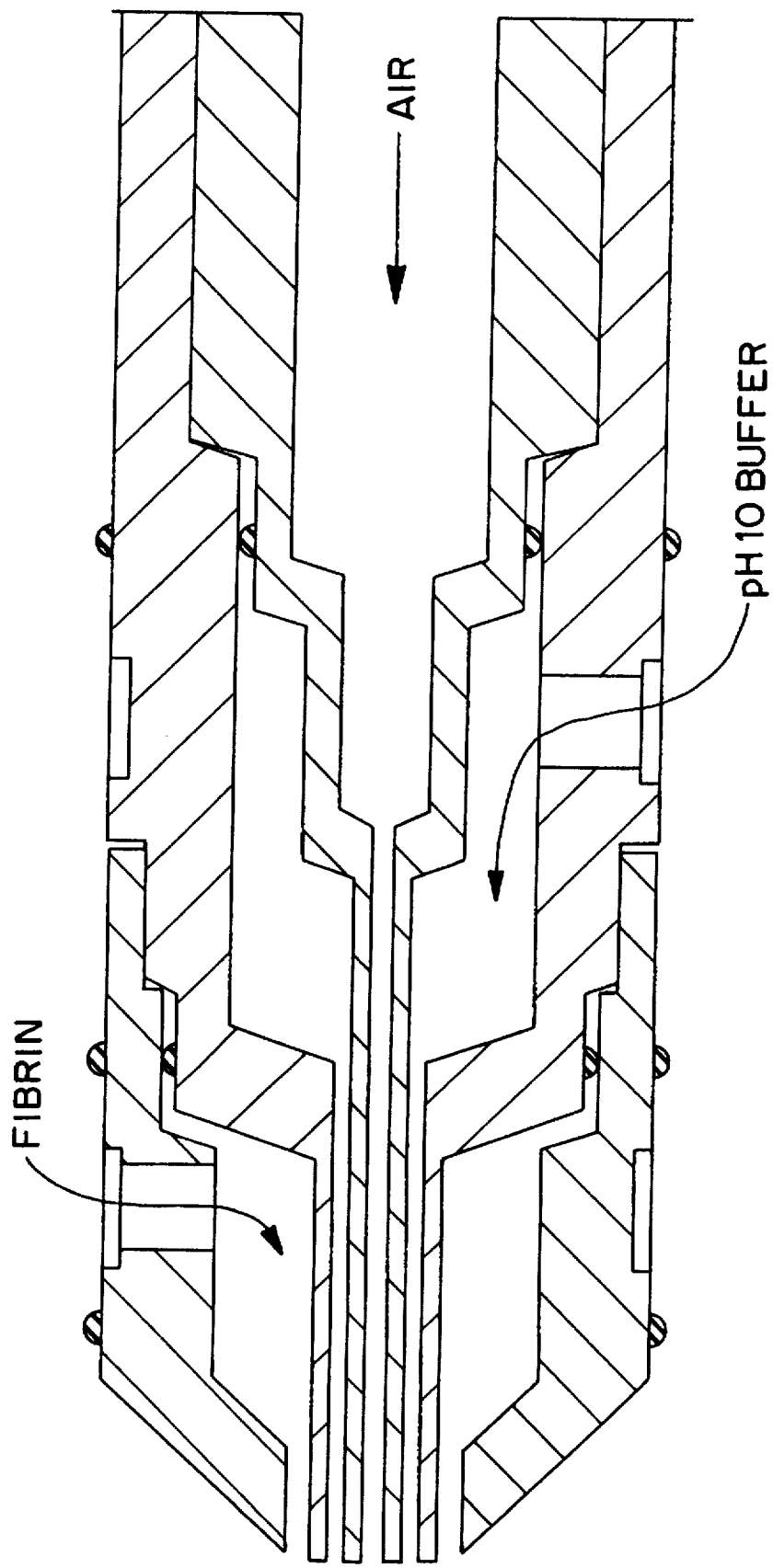
FIG. 2 is a lateral crossectional view of the present spray head

The exit surface of the a spray head of the present invention is shown generally as 10 in FIG. 1. The central aperture 12 preferably is employed to discharge the gas, although it could also be used alternatively for one of the fibrin sealant forming components. A first annular aperture 14 is concentric with and spaced radially outward from the central aperture 12. Preferably, one of the components is discharged through the first annular aperture 14 and most preferably the pH buffer component is discharged. The second annular aperture 16 is shown concentric with and spaced radially outward from the other two apertures. This second annular aperture 16 is preferably used to discharge the fibrin monomer containing solution.

Suitable dimensions for the apertures can be any convenient dimensions to the skilled person in the art and may be dependent upon the components. It is preferred that the central aperture have a diameter of from about 0.15 to about 0.35 and most preferably 0.30 mm. Preferably, the inner diameter of the first annular aperture is from about 0.75 to 0.85 mm and the outer diameter of the first annular aperture is from about 1.0 to 1.25 mm. Preferably, the inner diameter for the second annular aperture is from about 1.35 to about 1.55 mm and the outer diameter is from about 1.80 to about 2.0 mm.

Any other components and suitable business can be employed in the present method and device without departing from the scope of the present invention.

I claim:

1. A device for applying a fibrin sealant comprising two components which will form said sealant when combined, which device comprises commonly actuable reservoirs for each of said components and a source of gas, wherein each of said reservoirs and said gas in separate fluid communication via a discrete channel to a spray head, said spray head having a first aperture located centrally in an exit end of said spray head through which said gas is discharged, said spray head having a first annular aperture in the exit end of said spray head within first annular aperture is concentric with said first aperture and through which one of said fibrin-sealant-forming components is discharged, and a second annular aperture in the exit end of said spray head being concentric with said first aperture and concentric with, and having a radius larger than said first annular aperture through which the second of said fibrin-sealant-forming components is discharged wherein all of said apertures are in a common plane.

2. A method for applying two components of a fibrin sealant which method comprises a simultaneous discharge from a spray head of a fibrin sealant applicator of a gas vehicle through a center hole in an exit end and centrally located within said spray head; a first fibrin sealant forming component through a first annular aperture concentric with and spaced radially outward from said center hole; and a second fibrin sealant forming component through a second annular aperture concentric with and spaced radially outward from said center hole and said first annular aperture, whereby a uniform efficient application of the components to form a uniform fibrin sealant is provided.

3. The method of claim 2 wherein a fibrin-monomer containing solution is discharged from said second annular aperture and a buffer solution suitable for providing polymerization and crosslinking of said fibrin monomer into a fibrin II crosslinked polymer sealant is discharged from said first annular aperture.

\* \* \* \* \*